US007648700B2

(12) United States Patent
Vignery et al.

(10) Patent No.: US 7,648,700 B2
(45) Date of Patent: *Jan. 19, 2010

(54) METHOD FOR FOSTERING BONE FORMATION AND PRESERVATION

(75) Inventors: Agnes Vignery, Branford, CT (US); Nozer M. Mehta, Randolph, NJ (US); James P. Gilligan, Union, NJ (US)

(73) Assignees: Unigene Laboratories, Inc., Boonton, NJ (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/839,957

(22) Filed: Aug. 16, 2007

(65) Prior Publication Data

US 2008/0057051 A1 Mar. 6, 2008

Related U.S. Application Data

(62) Division of application No. 11/128,095, filed on May 11, 2005.

(60) Provisional application No. 60/571,200, filed on May 14, 2004.

(51) Int. Cl.
*A01N 63/00* (2006.01)
*A61K 38/00* (2006.01)
*A61F 2/02* (2006.01)

(52) U.S. Cl. ............... 424/93.7; 514/12; 623/11.11; 623/13.12; 623/17.17

(58) Field of Classification Search ............... 424/93.7; 514/12; 623/11.11, 13.12, 17.17
See application file for complete search history.

(56) References Cited

U.S. PATENT DOCUMENTS

| | | | | |
|---|---|---|---|---|
| 3,228,393 | A | 1/1966 | Michele | 128/92 |
| 3,605,123 | A | 9/1971 | Hahn | 3/1 |
| 4,608,052 | A | 8/1986 | Van Kampen et al. | 623/22 |
| 5,108,435 | A | 4/1992 | Gustavson et al. | 623/16 |
| 5,192,324 | A | 3/1993 | Kenna | 623/16 |
| 5,263,986 | A | 11/1993 | Noiles et al. | 623/16 |
| 5,358,533 | A | 10/1994 | Noiles et al. | 623/22 |
| 5,441,537 | A | 8/1995 | Kenna et al. | 419/2 |
| 5,489,306 | A | 2/1996 | Gorski | 623/16 |
| 5,510,370 | A | 4/1996 | Hock | 514/443 |
| 5,789,234 | A | 8/1998 | Bertelsen et al. | 435/354 |
| 6,103,495 | A | 8/2000 | Mehta et al. | 435/69.1 |
| 6,319,685 | B1 | 11/2001 | Gilligan et al. | 435/68.1 |
| 6,362,231 | B1 | 3/2002 | Sakai et al. | 514/654 |
| 6,376,476 | B1 | 4/2002 | Gasper et al. | 514/100 |
| 6,395,919 | B1 | 5/2002 | Bhatnagar et al. | 558/414 |
| 6,432,656 | B1 | 8/2002 | Del Mar et al. | 435/7.21 |
| 6,521,667 | B1 | 2/2003 | Del Mar et al. | 514/653 |
| 6,620,332 | B2 | 9/2003 | Amrich | 216/11 |
| 6,682,567 | B1 | 1/2004 | Schroeder | 623/22.24 |
| 6,758,849 | B1 | 7/2004 | Michelson | 606/61 |
| 2004/0033950 | A1 | 2/2004 | Hock et al. | 514/12 |

FOREIGN PATENT DOCUMENTS

WO  WO 03/039331  5/2003

OTHER PUBLICATIONS

U.S. Appl. No. 11/128,095, filed May 11, 2005, Agnes Vignery et al.
U.S. Appl. No. 11/839,993, filed Aug. 16, 2007, Agnes Vignery et al.
Suva, et al., "Pattern of Gene Expression Following Rat Tibial Marrow Ablation", *Journal of Bone and Mineral Research*, 8(3):379-388 (1993).
Shimizu, et al., "Sequential Expression of Bone Morphogenetic Protein, Tumor Necrosis Factor, and Their Receptors in Bone-Forming Reaction After Mouse Femoral Marrow Ablation", *Bone*, 23(2):127-133 (1998).
Yamashita, et al., "Retardation in Bone Resorption after Bone Marrow Ablation in *Klotho* Mutant Mice", *Endocrinology*, 141(1):438-445 (2000).
Tanaka, et al., "Local and Systemic Expression of Insulin-like Growth Factor-I (IGF-I) mRNAs in Rat after Bone Marrow Ablation", *Biochemical and Biophysical Research Communications*, 287(5):1157-1162 (2001).
Tanaka, et al., "Effect of IGF-I and PDGF administered in vivo on the expression of osteoblast-related genes in old rats", *Journal of Endocrinoolgy*, 174(1):63-70 (2002).
Tanaka, et al., "Effects of basic fibroblast growth factor on osteoblast-related gene expresson in the process of medullary bone formation induced in rat femur", *Journal of Bone and Mineral Metabolism*, 21:74-79 (2003).
Chen, et al., "Biglycan-Deficient Mice Have Delayed Osteogenesis after Marrow Ablation", *Calcified Tissue International*, 72(5):577-582 (2003).
Andreassen, et al., "Intermittent Parathyroid Hormone (1-34) Treatment Increases Callus Formation and Mechanical Strength of Healing Rat Fractures", *Journal of Bone and Mineral Research*, 14:960-968 (1999).

(Continued)

*Primary Examiner*—Jon P Weber
*Assistant Examiner*—Abdel A Mohamed

(57) ABSTRACT

A method of inducing bone formation in a subject in need of such inducement comprises the steps of mechanically inducing an increase in osteoblast activity in the subject and elevating blood concentration of at least one bone anabolic agent in the subject. The method steps may be performed in any order, but in sufficient time proximity that the elevated concentration of the anabolic agent and the mechanically induced increase in osteoblast activity overlaps. The method may additionally comprise providing the subject with an elevated blood concentration of at least one antiresorptive agent, wherein the elevated concentration is sufficient to prevent resorption of new bone growth produced due to the osteoblast activity. Use of the method permits targeting of specific bones of the subject for bone production and preservation, faster bone production and earlier discontinuation of bone anabolic pharmaceuticals. Kits adapted for performing the method are provided.

12 Claims, 8 Drawing Sheets

OTHER PUBLICATIONS

Figure 3A:
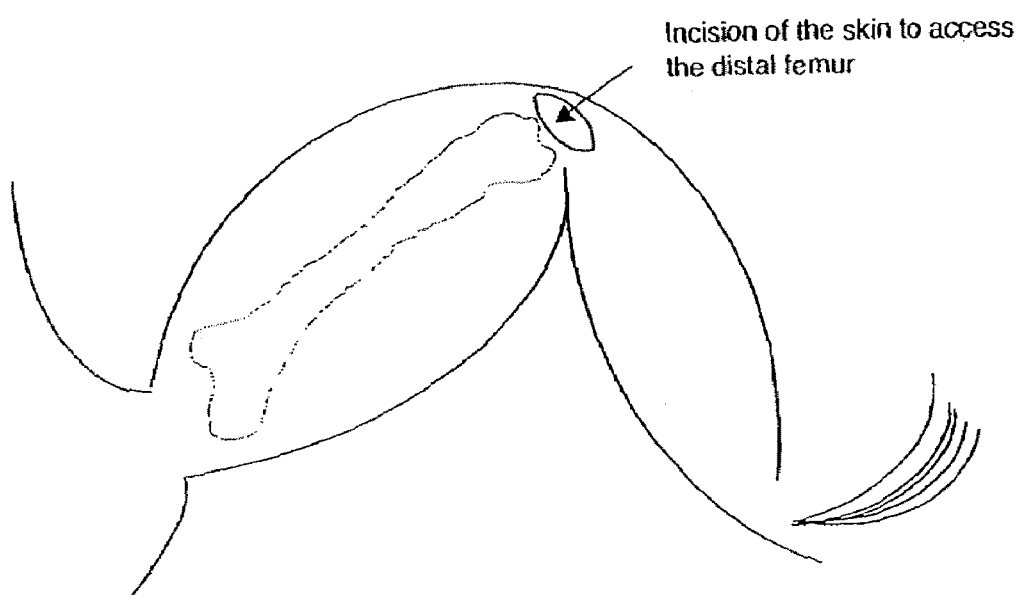

Nakajima, et al., Mechanisms for the Enhancement of Fracture Healing in Rats Treated With Intermittent Low-Dose Human Parathyroid Hormone (1-34), *Journal of Bone and Mineral Research*, 17:2038-2047 (2002).

Whitfield, et al. "Parathyroid Hormone, Its Fragments and Their Analogs for the Treatment of Osteoporosis", *Treatment in Endocrinology*, 2002, vol. 3, pp. 175-190.

Skripitz et al. Strong Effect of PTH (1-34) on Regenerating Bone. A Time Sequence Study in Rats. *ACTA Orthop. Scand.*, 2000, vol. 71, No. 6, pp. 619-624.

Reginster et al. "Strontium Ranelate: A New Paradigm in the Treatment of Osteoporosis" Expert Opin. Investig. Drugs, 2004, vol. 13, No. 7, pp. 857-864.

U.S. Appl. No. 11/430,752, filed May 9, 2006, Vignery et al.
U.S. Appl. No. 11/267,987, filed Nov. 7, 2005, Vignery et al.
Voelker, *JAMA* (1998), vol. 280, p. 315.
U.S. Appl. No. 12/059,662, filed Mar. 31, 2008, Agnes Vignery et al.
U.S. Appl. No. 12/059,605, filed Mar. 31, 2008, Agnes Vignery et al.
U.S. Appl. No. 11/267,987, filed Nov. 7, 2005, Agnes Vignery et al.
U.S. Appl. No. 11/254,640, filed Oct. 21, 2005, Murphy et al.

Hunziker, J. et al., "Mandibular bone formation rates in aged ovariectomized rats treated with anti-resorptive agents alone and in combination with intermittent parathyroid hormone", Journal of Dental Research, vol. 79, No. 6, Jun. 2000, pp. 1431-1438.

Nemeth, E. et al., "Calcilytic compounds: Potent and selective Ca2+ receptor antagonists that stimulate secretion of parathyroid hormone", Journal of Pharmacology and Experimental Therapeutics, vol. 299, No. 1, Oct. 2001, pp. 323-331.

Skripitz et al., "Implant fixation enhanced by intermittent treatment with parathyroid hormone", Journal of Bone and Joint Surgery, British Volume, Livingstone, London GB, vol. 83-B, No. 3, Apr. 2001, pp. 437-440.

Skripitz, R. et al., "Parathyroid hormone increases attachment of PMMA cement to bone", Journal of Orthopaedic Science: Official Journal of the Japanese orthopaedic Association 2001, vol. 6, No. 6, 2001, pp. 540-544.

Kobayashi, S. et al., "Advantages of concurrent use of anabolic and antiresorptive agents over single use of these agents in increasing trabecular bone volume, connectivity and biomechanical competence of rat vertebrae", Bone, vol. 25, No. 6, Dec. 1999, pp. 703-712.

Supplementary European Search Report dated Aug. 25, 2009 corresponding to European Patent Application No. 05760624.6.

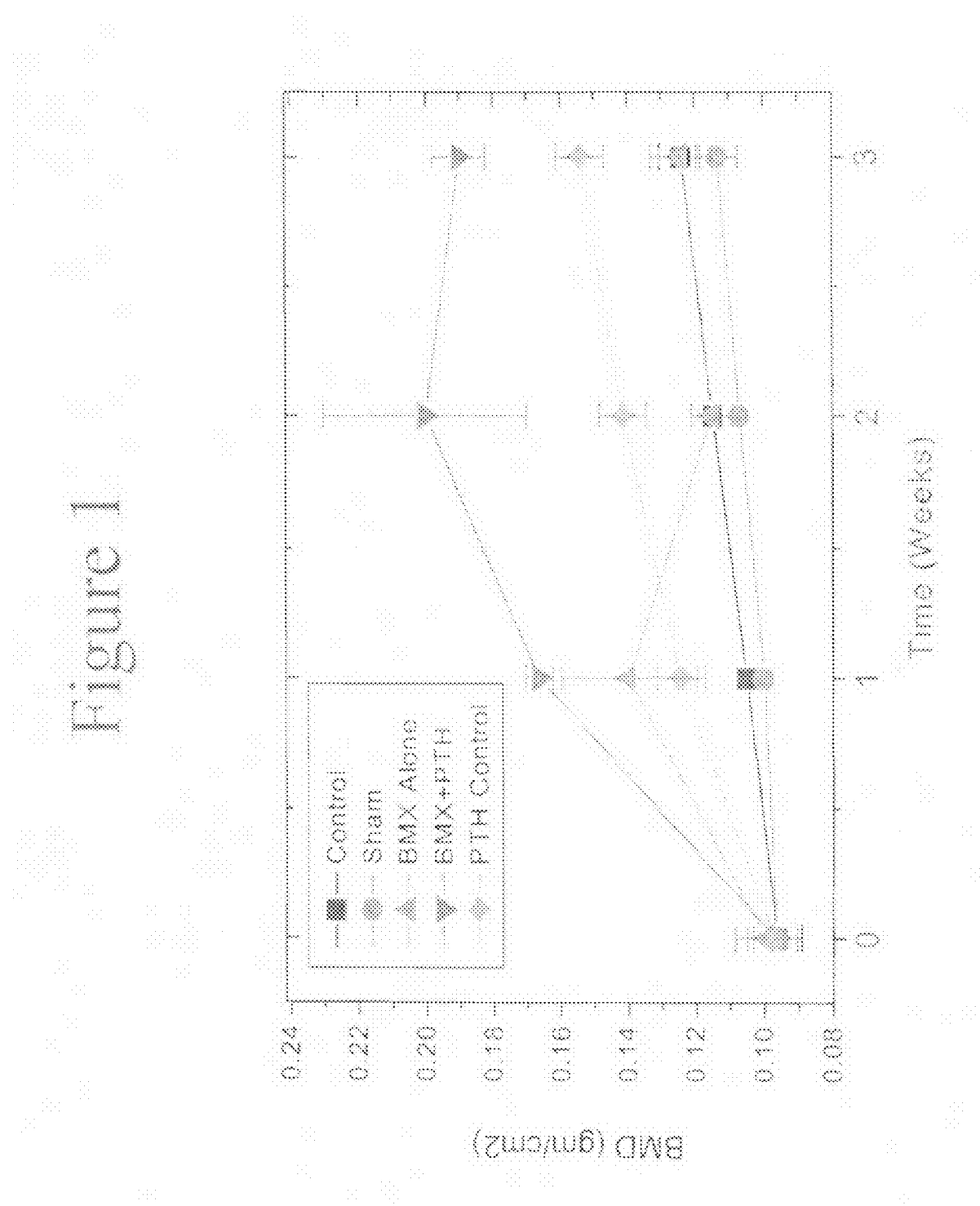

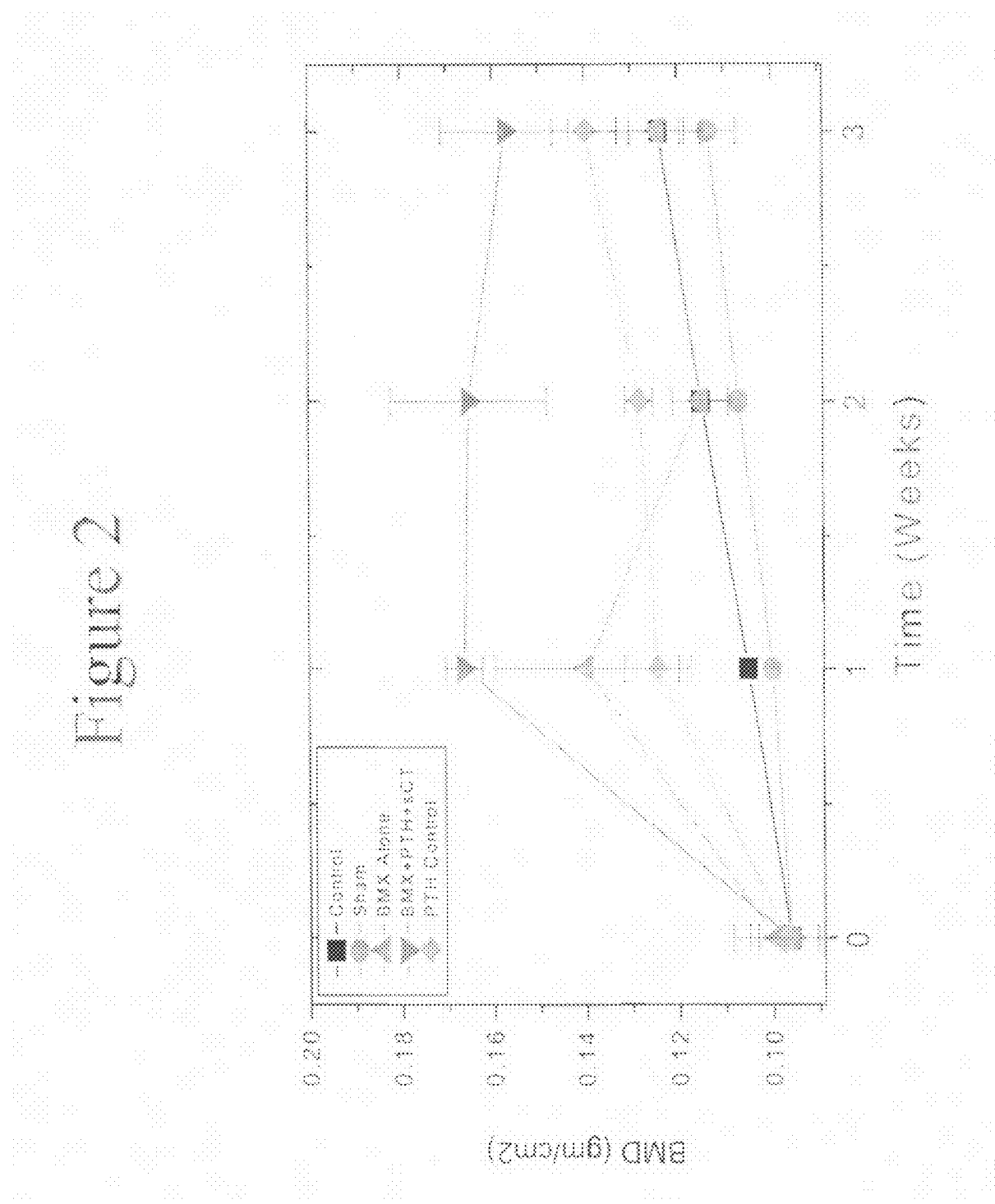

COMPARISON OF PTH 1-31NH$_2$, PTH 1-34NH$_2$ AND PTH1-34-OH

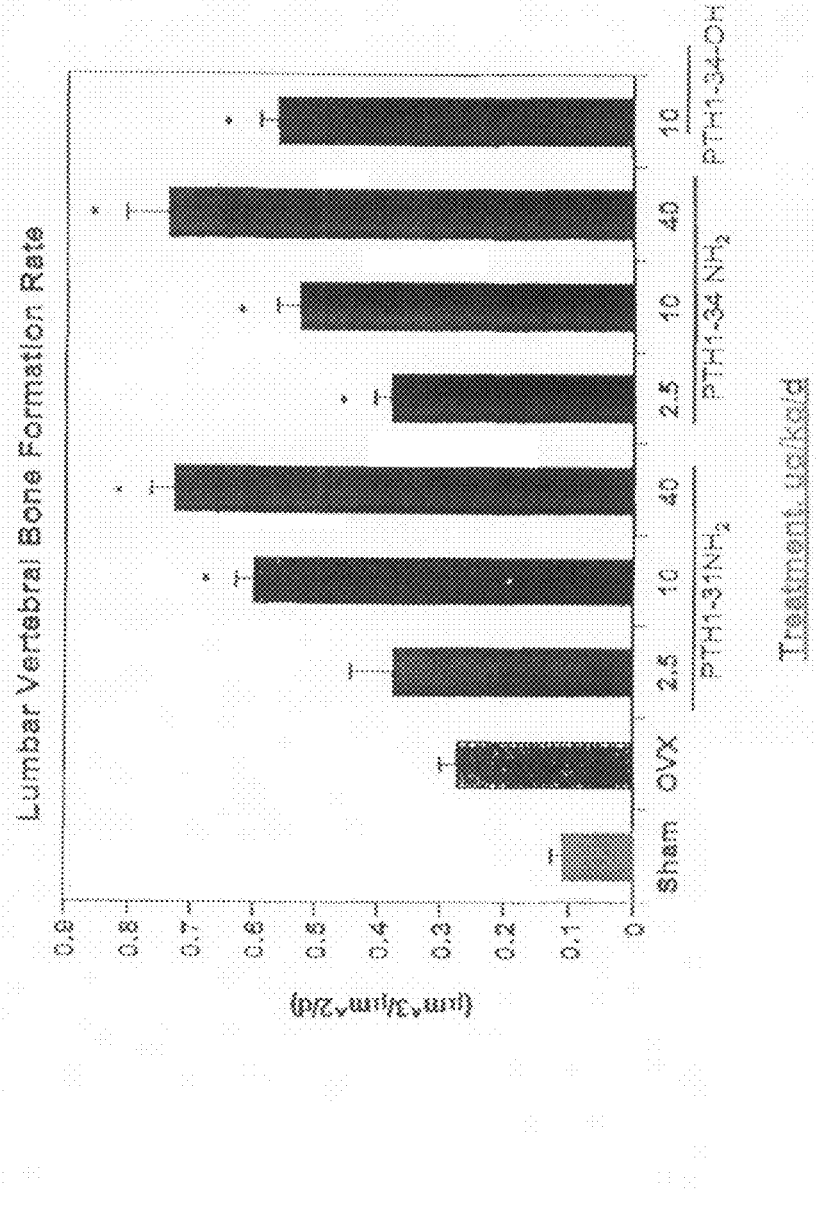

METHOD FOR FOSTERING BONE FORMATION AND PRESERVATION

CROSS-REFERENCE TO RELATED APPLICATIONS

The present application is a divisional of U.S. patent application Ser. No. 11/128,095, filed May 11, 2005, which is a 35 U.S.C. §119 conversion of U.S. Provisional Application No. 60/571,200, filed May 14, 2004, the contents of which are specifically incorporated herein.

STATEMENT REGARDING FEDERALLY SPONSORED RESEARCH OR DEVELOPMENT

The invention disclosed herein was made with Government support under NIH Grant No. DE 12110 from the National Institutes of Health. Accordingly, the government has certain rights in this invention.

FIELD OF THE INVENTION

The present invention relates generally to a method for fostering bone formation in a subject. More particularly the invention concerns a method for inducing rapid bone formation and then preserving the bone thus produced, e.g., by minimizing its resorption. The invention permits specific targeting of particular bones of a subject for repair, strengthening, reshaping and/or modeling. The invention is additionally directed to a kit for carrying out the method of the invention.

BACKGROUND OF THE INVENTION

Bones are multi-purpose structures that play diverse, vital roles in vertebrates. They provide a framework that supports the body and gives it shape. Bone undergoes a continuous renewal or remodeling during the lifetime of an individual. Bone consists of living cells widely scattered within a non-living material known as matrix. Two main types of cells are responsible for bone remodeling: the osteoblasts involved in bone formation and the osteoclasts involved in bone resorption. The matrix is formed by the action of osteoblasts, that make and secrete bone matrix proteins such as collagen, which provide elasticity, as well as mineral salts formed from calcium and phosphorous, which impart hardness to bone. As bone tissue matures, some osteoblasts are trapped in the bone matrix and differentiate into osteocytes, which are mature bone cells that carry out normal cellular activities. These osteocytes connect with other osteocytes through the bone matrix and can sense pressure or cracks in the bone. They therefore assist in directing where osteoclasts will act to dissolve bone during the repair and/or regeneration of bone.

Osteoclasts are cells that dissolve existing bone, thus facilitating bone growth, repair and regeneration. Osteoclasts are multinucleated cells that originate from the fusion of mononuclear phagocytes. Osteoclasts secrete protons that lower the pH of an extracellular compartment located between osteoclasts and bone. This low pH facilitates the dissolution of bone crystals and activates lysosomal enzymes that digest the bone matrix. Osteoclasts are therefore powerful and efficient bone resorbing cells that cover only 0.5% of the bone surface. With regard to bone formation, osteoblasts produce a structure, known as "osteoid", which is formed of bone collagen and other proteins. The osteoblasts thereafter control the deposition of calcium and other minerals into the osteoid in order to produce the calcified bone tissue. Upon the completion of bone formation, the osteoblasts flatten out and form a lining upon the surface of the bone. These flattened osteoblasts, known as "lining cells", regulate passage of calcium into and out of the bone. In addition, they produce, upon hormonal activation, proteins that promote osteoblast differentiation and activation. Making new bone is therefore a slow process that requires the lying down of the osteoid, its maturation and then its calcification. In contrast to osteoclasts, osteoblasts cover 30% of the bone surface.

The bones of the skeleton are not entirely solid throughout. The outside, i.e., cortical, bone is substantially solid throughout, having only a few small canals. Located inwardly from the cortical bone, however, is spongy bone known as cancellous bone. The cancellous bone is composed of a honeycomb network of trabecular bone defining a plurality of spaces or cavities filled with fluid bone marrow, stem cells and some fat cells. Existing within these bone marrow cavities are, inter alia, various highly specialized cells which assist in breaking down existing bone and correspondingly producing new bone to replace that which is broken down or which may be otherwise lost due to injury or illnesses such as osteoporosis.

The physical structure of bone may be compromised by a variety of factors, including disease and injury. One of the most common bone diseases is osteoporosis, which is characterized by low bone mass and structural deterioration of bone tissue, leading to bone fragility and an increased susceptibility to fractures, particularly of the hip, spine and wrist. Osteoporosis develops when bone resorption occurs too rapidly, if bone replacement occurs too slowly, or due to a combination of both. This is in part due to the fact that it requires six months for osteoblasts to rebuild the amount of bone destroyed by osteoclasts in three days. Bone injury, on the other hand, involves localized trauma to the bone.

A variety of methods are well-known in the art for fostering bone formation in individuals who (1) suffer from diminished bone mass due, for example, to illness, (2) are subjected to bone trauma causing injury such as bone fractures, and (3) need to strengthen bone, such as vertebral bones. Such prior art methods for treating these disorders are typically systemic in nature, however. That is, they treat the whole skeleton as a single entity. These methods are therefore not commonly able to be targeted on one or more specific bones, e.g., those of the hip, shoulder, spine and/or wrist, which may require a more focused treatment due to bone losses due to disease effects caused by, e.g., osteoporosis or by bone trauma such as that due to a fracture. Moreover, prior art methods frequently require undesirably long treatment regimens, with accompanying patient compliance problems.

There has thus been a long-felt need by those working in this field for a faster and more targeted method of inducing bone formation in subjects suffering from diminished bone mass, especially for a method coupled with an enhancement in retention of the new bone so produced. The present invention permits, in addition to the general systemic effect noted above, specific targeting of one or more particular bones or bony areas most in need of such treatment for rapid bone formation. As explained below, the method and kit of the present invention are particularly adapted to provide more effective bone formation with increased rapidity while permitting the retention of the bone thus produced and thus to admirably fulfil the desired functions.

SUMMARY OF THE INVENTION

It is therefore an object of the present invention to provide a method for inducing rapid bone formation in a subject such that the length of treatment with a bone anabolic agent may be reduced, thus offering safety and pharmacoeconomic advantages.

It is also an object of the present invention to provide a method for inducing bone formation at a rapid rate in a subject suffering from diminished bone mass which permits specific bones of the subject to be targeted for an increase in bone mass, while additionally providing beneficial bone formation effects to the entire skeleton of the subject.

It is another object of the invention to provide a method capable of inducing rapid bone formation in subjects so as to prevent and/or treat bone fractures.

It is a further object of the invention to provide a method capable of inducing rapid bone formation in subjects requiring such additional bone to serve as an anchoring mechanism for prostheses of, e.g., the hip, knee and shoulder and/or other types of implants such as dental implants.

It is a still further object of the invention to provide a method capable of inducing rapid bone formation in subjects requiring bone strengthening to alleviate chronic pain due to conditions such as vertebral crush.

It is yet another object of the invention to provide a method capable of diminishing resorption of any substantial portion of such additional bone thus produced in accordance with the invention.

It is another object of the invention to provide a method capable of inducing rapid bone formation so as to permit bone reshaping/modeling via said additional bone formation.

It is a further object of the invention to provide an article of manufacture comprising a kit adapted to enable one to carry out the above-described method of the invention.

In a preferred embodiment, the method of the invention is utilized with a human subject. However, the invention additionally contemplates veterinary applications.

In one embodiment, the invention provides a method of inducing bone formation in a subject in need of such inducement comprising the steps of (a) mechanically inducing an increase in osteoblast activity in the subject; and (b) elevating blood concentration of at least one bone anabolic agent therein, e.g., by administering such an agent or by administering a compound which causes natural formation of such an agent. The aforesaid steps may be performed in any order, but in sufficient time proximity that the elevated concentration of the anabolic agent and the mechanically induced increase in osteoblast activity at least partially overlaps.

In a further embodiment of the invention the method comprises the steps of targeting for treatment at least one bone of the subject, wherein each such targeted bone defines a bone marrow cavity therein. The bone marrow cavity contains, inter alia, a quantity of bone marrow and a plurality of osteoblasts. The method further comprises mechanically altering the contents of the bone marrow cavity to thereby stimulate and thus increase osteoblast differentiation and/or activity therein. The method additionally comprises administering to the subject at least one bone anabolic agent for a duration and at a concentration sufficient to raise blood levels of the anabolic agent within the subject above natural levels thereof and thereby prolong the mechanically induced osteoblast activity. The mechanical alteration of the contents of the bone marrow cavity in bones wherein it is desired to foster such bone growth permits specific bones of the subject to be particularly targeted for inducing bone formation therein.

The invention further provides a method of inducing bone formation in a subject suffering from diminished bone mass which comprises the steps of targeting for treatment at least one bone of the subject, wherein each targeted bone defines a bone marrow cavity therein. The bone marrow cavity contains a quantity of bone marrow and a plurality of osteoblasts. The method of the invention further comprises mechanically altering the contents of the bone marrow cavity to thereby stimulate and thus increase osteoblast activity (e.g., increased differentiation or increased bone formation by stimulating osteoblasts) therein. Thereafter, bone mass is increased within the cavity due to the increased osteoblast activity. The method additionally comprises administering to the subject at least one bone anabolic agent for a duration and at a concentration sufficient to raise blood levels of the anabolic agent within the subject above natural levels thereof and thereby prolong the mechanically induced osteoblast activity. The method, however, further comprises additionally administering, either (1) contemporaneous with, (2) overlapping with, or (3) subsequent to the administration of the bone anabolic agent, an antiresorptive agent for a duration and at a concentration sufficient to diminish resorption of new bone produced due to the osteoblast activity. As with the method described above, the mechanical alteration of the contents of the bone marrow cavity of bones in which such stimulated growth is desired thus permits specific bones of the subject to be particularly targeted for enhanced bone formation.

The invention additionally provides a kit for fostering bone formation in at least one targeted bone of a subject in need of such bone formation. The kit includes at least one container having therein at least one bone anabolic agent, as well as a mechanical alteration device for altering contents of a bone marrow cavity in at least one targeted bone. The kit may additionally be provided with an evacuation device for evacuating at least a portion of the contents from the bone marrow cavity.

BRIEF DESCRIPTION OF THE DRAWING(S)

Figure 3B:
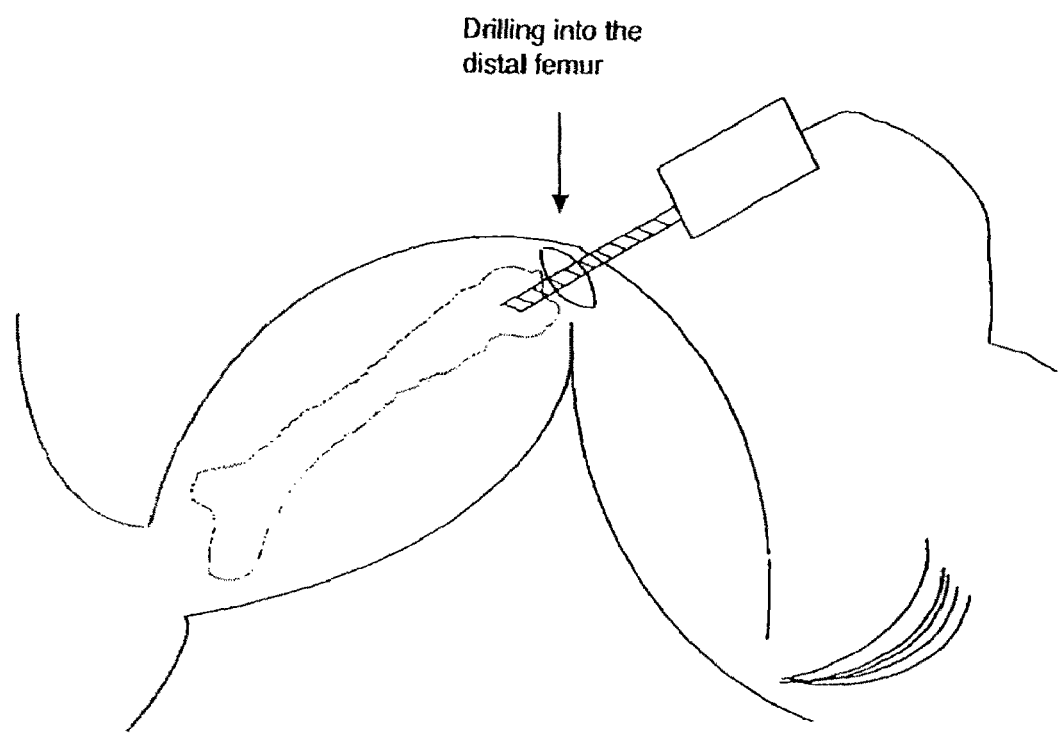
Figure 3C:
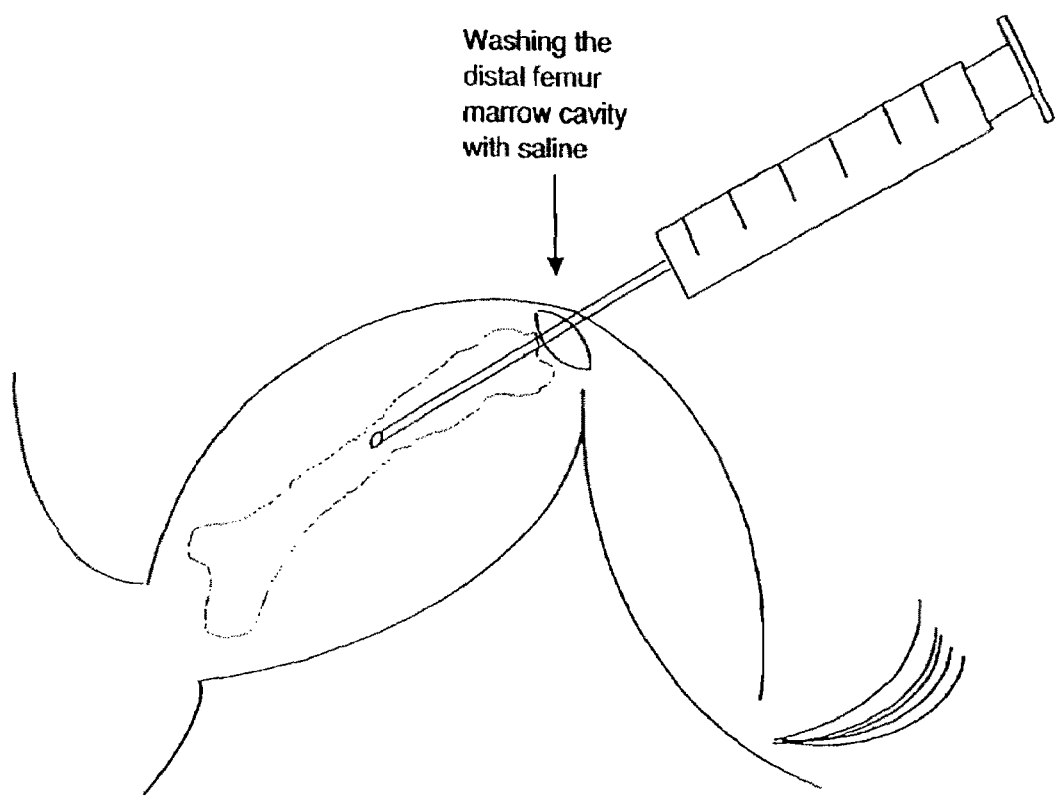
Figure 3D:
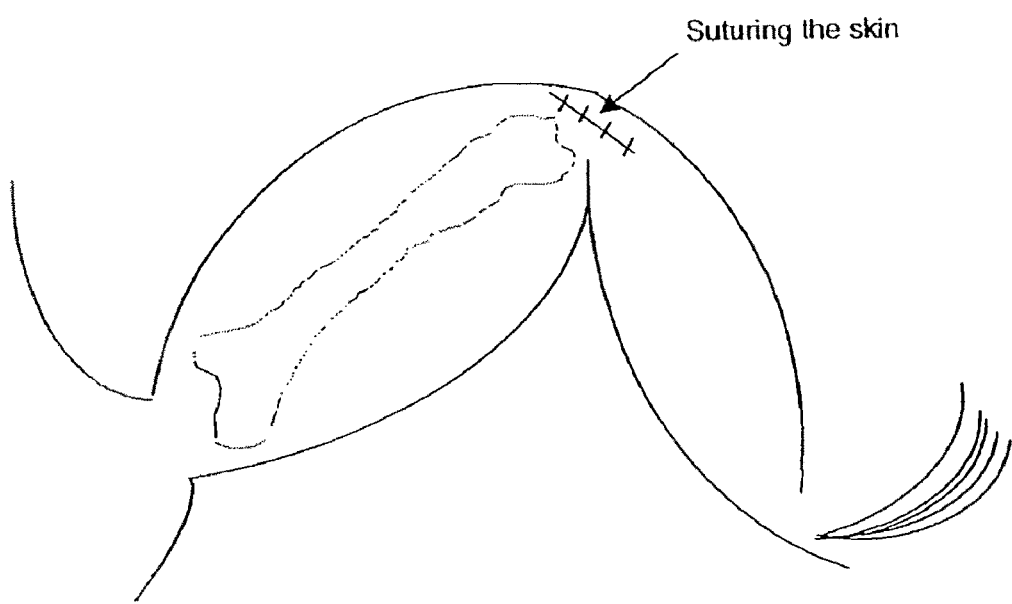
Figure 4:
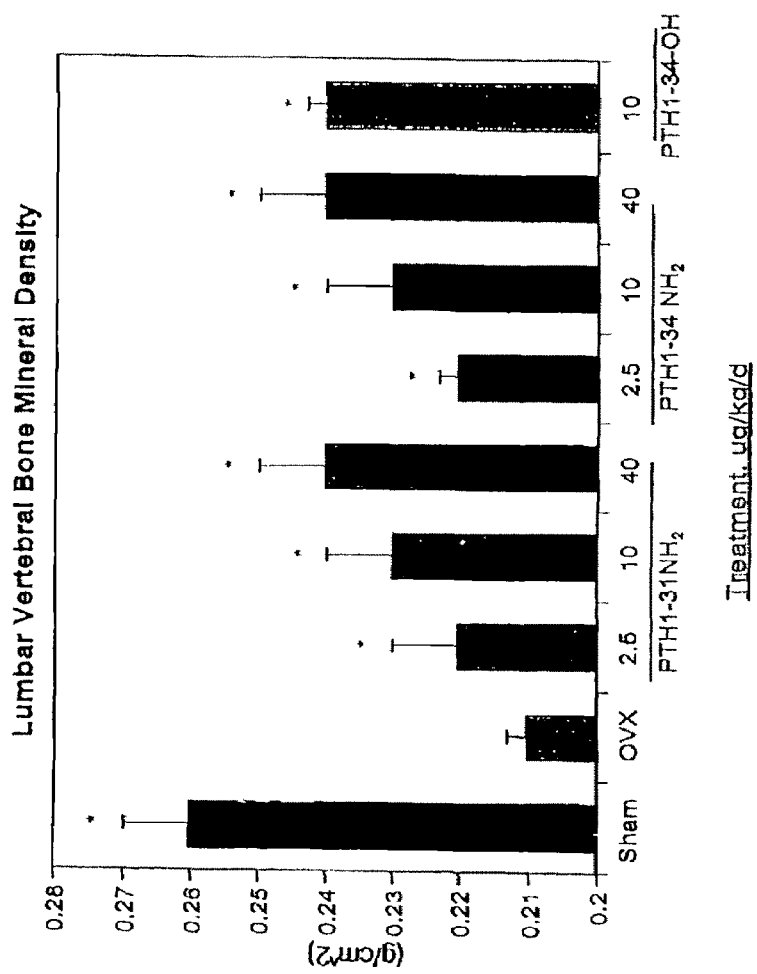

FIG. 1 is a graphical representation of the results of a PIXIMUS analysis of the femur distal marrow cavity bone mineral density ("BMD") of groups of laboratory rats tested at one-week intervals during a three-week test regimen. The PIXIMUS analyzer is available from Lunar Corp., Palo Alto, Calif. and provides Dual Energy X-Ray Absorptiometry ("DEXA") data for small animals such as mice and rats. Male Sprague-Dawley rats (5 animals per group) aged 9 weeks were sacrificed and tested at time 0 and after 1, 2 and 3 weeks. The various groups were subjected to the following treatment modalities: Group A—left femur control; Group B—left femur sham; Group C—mechanical bone marrow ablation (bmx) to alter the contents of the bone marrow cavity of the left femur; Group D—mechanical bone marrow ablation treatment (bmx) of the left femur, coupled with the administration of an amidated parathyroid hormone truncate (PTH [1-34]-$NH_2$) during days 1-21; and Group E—a right (non-bmx) femur BMD measurement of rats treated during days 1-21 with an amidated parathyroid hormone truncate (PTH [1-34]-$NH_2$) wherein the rat's left femur had undergone a bone ablation (bmx) treatment;

FIG. 2 is a graphical representation of the results of a PIXIMUS analysis of the femur distal marrow cavity BMD of a second set of groups of male Sprague-Dawley rats (5 animals per group) aged 9 weeks which were sacrificed and tested at time 0 and after 1, 2 and 3 weeks. The various groups were subjected to the following treatment modalities: Group F—left femur control; Group G—left femur sham; Group H—mechanical bone marrow ablation (bmx) to alter the contents of the bone marrow cavity of the left femur; Group I—mechanical bone marrow ablation (bmx) of the left femur, coupled with administration of an amidated parathyroid hormone truncate (PTH[1-34]-$NH_2$) during days 1-7, followed by the administration of a salmon calcitonin (sCT) antiresorptive agent during days 7-21; and Group J—a right femur BMD measurement of rats treated with an amidated parathyroid hormone truncate (PTH[1-34]-$NH_2$) wherein the rat's left femur had undergone a bone marrow ablation (bmx) treatment;

FIGS. 3A-3D illustrate a representative series of steps for carrying out a left femur bone marrow ablation in a rat from one of Groups A-J discussed above. FIG. 3A) accessing the distal femur; FIG. 3B) drilling into the bone marrow cavity of the distal femur; FIG. 3C) washing the bone marrow cavity; and FIG. 3D) suturing the incision;

FIG. 4 is a bar graph comparing the Lumbar Vertebral Bone Mineral Density obtained in osteoporotic female Sprague-Dawley rats wherein the osteoporosis was induced via an ovariectomy. The rats were treated with (1) PTH[1-31]-$NH_2$; (2) PTH[1-34]-$NH_2$; and PTH[1-34]-OH; and FIG. 5 is a bar graph comparing the Lumbar Vertebral Bone Formation Rate obtained in osteoporotic female Sprague-Dawley rats wherein the osteoporosis was induced via an ovariectomy. The rats were treated with (1) PTH[1-31]-$NH_2$; (2) PTH[1-34]-$NH_2$; and PTH[1-34]-OH.

DETAILED DESCRIPTION OF PREFERRED EMBODIMENTS OF THE INVENTION

In a first embodiment the invention provides a method of inducing new bone formation in a subject in need of such inducement. The method comprises the steps of mechanically inducing an increase in osteoblast activity in the subject and elevating blood concentration of at least one bone anabolic agent in the subject. The above steps may be performed in any order, but are to be carried out in sufficient time proximity that the elevated concentration of the anabolic agent and the mechanically induced increase in osteoblast activity at least partially overlap.

Inducement of bone growth may include, for example, generating new or additional bone at locations where such bone growth is not presently taking place and/or stimulating the growth (i.e., increasing the rapidity thereof) of bone which is already in the process of formation. Without being bound in any way by theory, applicants believe that the inducement of bone growth takes place due to the combined effects of (1) a mechanical inducement of osteoblast activity in the subject coupled with (2) an elevation in the blood concentration of at least one bone anabolic agent therein.

Mechanical inducement of an increase in osteoblast activity may be obtained, in a preferred embodiment of the invention, by a process of bone marrow irrigation and ablation. Again, without being bound in any way by theory, applicants believe that the bone marrow irrigation and ablation process leads to the formation of a clot within the bone marrow cavity which, through a cascade of biochemical reactions, contributes to increasing osteoblast activity in the subject.

In an another embodiment, the increased osteoblast activity may alternately be obtained by coupling the mechanical inducement with an additional form of inducement such as biochemical inducement. Such biochemical inducement may be obtained by administering to the subject, for example, a quantity of a blood factor such as Factor ("F") VII, Factor VIIa or a combination thereof. Following tissue or vascular injury clotting is initiated by the binding of plasma FVII/FVIIa to tissue factor (tissue thromboplastin). This complex (FVII/FVIIa+Thromboplastin) initiates a sequence of events which leads to activation of the coagulation cascade ultimately leading to fibrin deposition and platelet activation. This complex sequence of events may contribute in part to the stimulation of osteoblasts in the bone marrow. Factors VII and VIIa are commercially available from Novo Nordisk.

The increase in osteoblast activity obtained with the use of the method of the invention may be due to a variety of factors including, but not necessarily limited to (1) osteoblast differentiation, i.e., the production of additional osteoblasts, (2) increasing the activity and/or effectiveness of osteoblasts which are already present in inducing bone formation in the subject, and (3) a combination thereof. In a preferred embodiment of the invention, the increase in osteoblast activity would include all of the above-noted functions.

In one embodiment, the blood concentration of the at least one bone anabolic agent may be elevated by direct administration of one or more bone anabolic agents to the subject.

In a further embodiment of the invention the method additionally comprises "targeting" one or more specific bones of the subject for inducement of bone growth. This targeting is accomplished by mechanically altering the contents of a bone marrow cavity within each targeted bone so as to induce the increased osteoblast activity therein.

The method of the invention is thus useful not only for bone repair, i.e., as in the case of a bone fracture due to trauma, but also for strengthening bone in a site-specific manner in the case of individuals shown by Dual Energy X-Ray Absorptiometry ("DEXA") or other techniques to require an increase in bone mass and/or density to prevent bone fractures, or who suffer due to bone weakness from chronic pain attributable to conditions such as vertebral crush. Moreover, as noted above, the method of the invention additionally serves to provide (and retain) new bone needed to serve as an anchor for prostheses such as artificial hips, knees and shoulders and/or for implants such as dental implants.

In a still further embodiment, the method of the invention additionally comprises providing the subject with an elevated blood concentration of at least one antiresorptive agent, wherein the elevated concentration is sufficient to diminish resorption of new bone growth produced due to the mechanically induced enhanced osteoblast activity according to the invention.

In one embodiment the invention provides a method of inducing bone formation in a subject in need of the same, wherein the method comprises (a) mechanically inducing an increase in osteoblast activity in the subject; and (b) administering to the subject at least one agent that causes elevated blood levels of an endogenous bone anabolic agent within the subject. The method steps may be performed in any order, but in sufficient time proximity that the elevated concentration of the anabolic agent and the mechanically induced increase in osteoblast activity at least partially overlaps. In one embodiment of the method, the agent causing an increased expression of the endogenous bone anabolic agent may be a calcilytic agent. Calcilytic agents useful with the method of the invention include, but are not limited to any agent that limits the binding of calcium to its receptor and thereby triggers the release of endogenous PTH. Examples of such calcilytic compounds are set forth in U.S. Pat. Nos. 6,362,231; 6,395,919; 6,432,656 and 6,521,667, the contents of which are incorporated herein by reference.

The invention additionally provides a method of inducing bone formation in a subject suffering from diminished bone mass or bone trauma. The method includes the step of targeting for treatment at least one bone of the subject, wherein each targeted bone defines a bone marrow cavity therein. The bone marrow cavity contains, inter alia, a quantity of bone marrow and a plurality of osteoblasts. The method of the invention further comprises mechanically altering the contents of the bone marrow cavity to thereby stimulate and thus increase osteoblast activity therein. The method additionally comprises administering to the subject at least one bone anabolic agent for a duration and at a concentration sufficient to raise blood levels of the anabolic agent within the subject above natural levels thereof and thereby prolong the mechanically induced osteoblast activity. For example, a bone anabolic agent endogenously produced in the human body is PTH[1-84] in the free acid form which is naturally found in levels of less than about 8 picomoles (pmoles) per liter in blood of a human subject. Thus the practice of the invention would involve, as indicated above, raising the blood levels of the bone anabolic agent within the subject to levels correspondingly above such natural level. Further to the above, the mechanical alteration of the contents of the bone marrow cavity thus permits specific bones of the subject to be targeted for enhanced bone formation.

In an embodiment of the invention, bone formation may be induced at a location of a long bone fracture in bone of the subject to increase the rapidity of healing of the fracture. In another embodiment, the method further comprises reshaping or modeling at least one targeted bone of a subject by inducing additional bone formation in a controlled manner thereon.

Applicants have surprisingly discovered that an initial burst of osteoblast activity can be sustained at unexpectedly high levels by elevating blood levels of a bone anabolic agent during a time that at least partially overlaps with the initial burst of osteoblast activity. This effect is demonstrated by comparing the curves obtained with Groups C and D in FIG. 1. Absent the bone anabolic agent, the initial burst of bone formation is quickly followed by the resorption of newly formed bone (see, e.g., the Group C curve in FIG. 1). The curve obtained with Group E of FIG. 1 shows that although increased bone growth is induced due to the administration of a PTH bone anabolic agent alone, this increase does not rise to the level achieved due to the coupling of bone marrow ablation (bmx) plus administration of PTH. The results set forth in FIG. 1 clearly demonstrate that the coupling of bmx and PTH administration provides an unexpected increase in degree, speed and longevity of bone formation relative to the effects of bmx or PTH alone, as well as a targeted site-specific response. Table 1 (below) sets forth the values upon which the curves obtained with Groups A-E in FIG. 1 are based. As no readings were taken for the Control (Group A) and Sham (Group B) groups at Week 1 and Week 2, these values were estimated for purposes of preparing the curves for these two Groups. Table 1, moreover, provides the standard deviations for the values obtained in each Group, which standard deviations are also indicated in FIG. 1.

bmx+PTH relative to PTH alone. This is due to the fact that the femur contains mostly cortical bone and the pQCT data (which has not yet been broken out into values corresponding to the various types of bone) presently is directed to an aggregate of all of the bone tissues.

FIG. 2 is provided to illustrate, inter alia, the further beneficial effect achieved due to the overlapping (i.e., with PTH administration) or subsequent administration of the antiresorptive agent salmon calcitonin (sCT). First, a comparison of the curves obtained with Group H (bmx alone) and Group J (PTH+sCT with no bmx) to that obtained with Group I (bmx+PTH+sCT) provide still further evidence of the synergistic effect attributable to the use of the method of the invention. Additionally, the curve obtained with Group I also demonstrates that the administration of the antiresorptive agent sCT following the initial burst of osteoblast activity which occurs due the coupling of bmx and PTH administration, significantly diminishes the proportion of the newly formed bone which is adsorbed into the subject's body due to the action of the osteoclasts. Table 2 (below) sets forth the values upon which the curves of FIG. 2 are based. As no readings were taken for the Control (Group F) and Sham (Group G) during

TABLE 1

BMD (DEXA) (gm/cm$^2$) ± standard deviation

| Groups | Femur | Week 0 | Week 1 | Week 2 | Week 3 |
|---|---|---|---|---|---|
| Control (Group A) | LEFT | 0.096 ± .007 | 0.105 | 0.115 | 0.124 ± .009 |
| Sham (Group B) | LEFT | 0.096 ± .007 | 0.1 | 0.107 | 0.113 ± .006 |
| BMX ALONE (Group C) | LEFT | 0.099 ± .009 | 0.140 ± .020 | 0.115 ± .006 | 0.124 ± .006 |
| BMX + PTH 1-21 (Group D) | LEFT | 0.096 ± .007 | 0.166 ± .004 | 0.200 ± .030 | 0.190 ± .008 |
| PTH 1-21 (Group E) | RIGHT | 0.097 ± .008 | 0.124 ± .007 | 0.141 ± .007 | 0.154 ± .007 |

Peripheral Quantitative Computerized Tomography ("pQCT") measurements taken by the inventors during the above-discussed experiments did not demonstrate an improvement in total bone content for the combination of Weeks 1 and 2, these values were estimated for purposes of preparing the curves. Table 2 provides the standard deviations for the values obtained in each Group, which standard deviations are also indicated in FIG. 2.

TABLE 2

BMD (DEXA) (gm/cm$^2$) ± standard deviation

| Groups | Femur | Week 0 | Week 1 | Week 2 | Week 3 |
|---|---|---|---|---|---|
| Control (Group F) * | LEFT | 0.096 ± .007 | 0.105 | 0.115 | 0.124 ± .009 |
| Sham (Group G) * | LEFT | 0.096 ± .007 | 0.1 | 0.107 | 0.113 ± .006 |
| BMX ALONE (Group H) * | LEFT | 0.099 ± .009 | 0.140 ± .020 | 0.115 ± .006 | 0.124 ± .006 |
| BMX + PTH 1-7 + sCT 7-21 (Group I) | LEFT | 0.096 ± .007 | 0.166 ± .004 | 0.165 ± .017 | 0.157 ± .014 |
| PTH 1-7 + sCT 7-21 (Group J) | RIGHT | 0.097 ± .008 | 0.124 ± .007 | 0.128 ± .003 | 0.140 ± .007 |

* Groups F, G and H are the same as Groups A, B and C (see Table 1).

The results set forth in FIGS. 1 and 2 and in corresponding Table 1 and Table 2 discussed above were obtained with the use of a method for mechanically inducing increased osteoblast activity as illustrated in FIGS. 3A-3D. The method shown in FIGS. 3A-3D is provided only for the purpose of illustration, however, and the invention is not limited to the procedure(s) illustrated in the indicated Figures since a number of alternate techniques, which would be well known to those of ordinary skill in the art, may be used to obtain the necessary mechanical induction of osteoblast activity. Thus, in the representative method illustrated in FIGS. 3A-3D, Male Sprague Dawley rats, 9 weeks old, i.e., at a rapid growth stage, were housed for 5-10 days prior to surgery (bmx). On the day of surgery, the rats were weighed and anesthetized with a combination of ketamine (50 mg/kg) and xylazine (10 mg/kg) using a decapione. The anesthetic was prepared by combining 0.4-0.8 ml Ketamine with 0.5 ml. Xylazine and 8.5 ml saline. The rats were each injected with the anesthetic at the rate of 0.1 ml/10 g body weight.

In preparation for surgery, the hair over the left knee joint of each rat was shaved. The shaved area was prepped with Betadine scrub and then washed with ethanol. A longitudinal 1.0 cm. incision was then made across the medial aspect of the knee joint (see FIG. 3A). The knee was then bent and the incised tissue was pulled back to expose the patella tendon as a landmark. The patella was pushed aside and a 1.0 mm hole was drilled through the femoral intracondylar notch above the tendon by a smooth 0.035 k-wire drill bit into the marrow cavity (see FIG. 3B). The drilling motion was repeated 5 times. Subsequently, the above-described drilling step was repeated using a threaded 0.045 inches drill bit.

Once the hole was completed, the contents of the bone marrow cavity were back-flushed by injecting 5 ml of normal saline solution into the femur using a syringe attached to a 26-gauge needle (see FIG.3C). The next step involved suturing the medial ligamentous structures with 4-0 Dexon thread and closing the skin incision with surgical metal clips (see FIG. 3D). Thereafter, each rat was injected with a 5 ml bolus of saline and tagged for identification. During recovery, the rats were given TYLENOL® brand acetaminophen solution (300 mg/kg/day) for the first 24 hours after surgery and then checked on a daily basis for the first 5 days.

On the day of sacrifice, each rat was euthanized in a $CO_2$ chamber. The rat's blood was then collected via a cardiac puncture. The femurs were removed and fixed in a 4% formalin solution, after which they were dehydrated in a graded series of ethanol solutions.

The bones were thereafter subjected to a variety of sample analysis techniques. These included X-ray analysis wherein the femurs were X-rayed in individually sealed plastic bags; PIXIMUS analysis using a Lunar PIXIMUS scanner to measure bone mineral density in the bone marrow cavity of the femurs; MicroCT analysis; and blood analysis for osteocalcin, PTH, CT, NTX and growth factors.

In one embodiment of the invention, the bone anabolic agent may be administered to the subject contemporaneous with the mechanical inducement of osteoblast activity (whether by increased osteoblast formation and/or by increased bone formation by pre-existing osteoblasts), which mechanical inducement may be achieved, e.g., by alteration of the bone marrow cavity. In preferred embodiments, marrow and/or other components of the marrow cavity is/are removed under pressure (e.g., by altering the relative pressure within versus without the marrow cavity).

In another embodiment the bone anabolic agent is administered subsequent to such mechanical inducement. In another embodiment the bone anabolic agent may be administered prior to mechanical inducement such that elevated levels of bone anabolic agent are already present at the time of mechanical inducement, which levels may then be maintained or continued intermittently for an extended period thereafter.

The bone anabolic agent may be administered orally, intravenously, intramuscularly, subcutaneously, via implant, transmucosally, transdermally, rectally, nasally, by depot injection or by inhalation and pulmonary absorption. In another embodiment the bone anabolic agent may be administered once as a time release formulation, a plurality of times, or over one or more extended periods. It is preferred that elevated blood levels of the anabolic agent be maintained at least intermittently for between about 14-365 days, and more preferably for between about 30-180 days, post-mechanical induction. Intermittent administration of parathyroid hormone, e.g., PTH[1-34]-$NH_2$, could occur once daily or once weekly resulting in peaks of blood concentration that return to baseline levels between doses, but nevertheless result in periodic elevated blood levels of a bone anabolic agent in a manner that overlaps the elevated osteoblast activity that is initially induced mechanically, although thereafter sustained, at least in part, by the anabolic agent.

In an additional embodiment the anabolic agent is selected from the group consisting of a parathyroid hormone (PTH), anabolic Vitamin D analogs, a low-density lipoprotein receptor-related protein 5 (LRP5), an activator of non-genomic estrogen-like signaling (ANGELS), a bone morphogenic protein (BMP), an insulin-like growth factor (IGF), a fibroblast growth factor (FGF), sclerostin, leptin, a prostaglandin, a statin, strontium, a growth hormone, a growth hormone releasing factor (GHRF), hepatocyte growth factor (HGF), calcitonin gene related peptide (CGRP), parathyroid hormone related peptide (PTHrP), transforming growth factor (TGF)-β1 and combinations thereof. As used herein, the term parathyroid hormone includes, but is not limited to natural parathyroid hormone, a truncate of natural parathyroid hormone, an amidated truncate of natural parathyroid hormone, an amidated natural parathyroid hormone and combinations thereof.

In one embodiment the bone anabolic agent is truncated PTH[1-34] in the free acid form. This material is commercially available in an FDA-approved pharmaceutical formulation from Eli Lilly & Co. under the trade mark FORTEO® (teriparatide). Other useful bone anabolic agents for use with the invention include, but are not limited to, an amidated truncate of natural parathyroid hormone, PTH[1-30]$NH_2$, PTH[1-31]$NH_2$, PTH[1-32]$NH_2$, PTH[1-33]$NH_2$, PTH[1-34]$NH_2$ and combinations thereof. In one preferred embodiment the bone anabolic agent is PTH[1-34]$NH_2$. Methods for the preparation of truncated parathyroid hormones are described in U.S. Pat. No. 6,103,495 to Mehta et al. Moreover, methodologies for amidating such truncated parathyroid hormones are provided in, for example, U.S. Pat. No. 5,789,234 to Bertelsen et al. and U.S. Pat. No. 6,319,685 to Gilligan et al. The contents of each of these patents is specifically incorporated herein by reference.

In one embodiment of the present method, a sufficient amount of the preferred truncated parathyroid hormone as discussed herein is administered to the subject to achieve, and thereafter maintain, a pulsatile blood concentration thereof in the subject of between about 50 and 350 pg/ml, preferably between about 100 and 200 pg/ml, and most preferably about 150 pg/ml. In another embodiment, the blood concentration of the parathyroid hormone in the subject is raised to its preferred level by no later than 7 days following mechanical alteration of the contents of the bone marrow cavity. As would be well known in this art, an appropriate dosage of the PTH bone anabolic agent must be calculated to achieve the above-indicated blood concentrations. In the case of injectable formulations, for example, the dose (in pure weight of the active hormone) given to, for example, a human subject, may be that taught in the literature relating to the bone anabolic activity of these various agents. Such dose may, but does not necessarily, range between about 10-200 µg, given once per day, more preferably between about 20-100 µg per dose and most preferably between about 20-50 µg per dose. Dosage levels of injectable formulations comprising bone anabolic agents other than the above-described parathyroid hormone-based agents would be consistent with those noted above for the PTH agents.

A series of experiments was performed comparing (1) lumbar vertebral bone mineral density, and (2) lumbar vertebral bone formation rate achieved with PTH[1-31]-NH$_2$ and PTH[1-34]-OH compared to the preferred PTH[1-34]-NH$_2$ analog discussed above in the absence of the mechanical induction step of the invention. The study involved a four-week treatment of female Sprague-Dawley rats at 10 months of age, and 6 months post-ovariectomy ("OVX"), which induces osteoporosis, with one of the three above-noted parathyroid hormone truncates. The rats were randomized into the following groups: sham OVX, OVX+vehicle, OVX+PTH [1-31]-NH$_2$ or PTH [1-34]-NH$_2$ (obtained from Unigene Laboratories, Inc.) at 2.5, 10 or 40 µg/kg/day subcutaneous, or PTH[1-34]-OH (obtained from Bachem) at 10 µg/kg/day subcutaneous. After 4 weeks of treatment, the right femur of each animal was analyzed by DEXA and bone histomorphometry. FIG. 4 is a bar graph providing a comparison of the lumbar vertebral bone mineral density achieved with PTH[1-31]-NH$_2$, PTH[1-34]-NH$_2$ and PTH[1-34]-OH. FIG. 5 is a bar graph comparing the lumbar vertebral formation rates achieved with these same truncates. Based on the results of these experiments it was determined that the bone anabolic activity of each of these analogs of PTH is substantially equivalent. Because of the similarity of anabolic action among the above-discussed parathyroid hormones, it is therefore reasonable to expect that all known PTH analogs will advantageously function in the desired manner in the method of the present invention.

In a further embodiment of the invention the mechanical induction of osteoblast activity is accomplished by inserting, into a bone marrow cavity of a bone targeted for enhanced bone formation, an object configured or adapted to physically alter the contents of the cavity and thereby to stimulate the osteoblast activity within the cavity. In another embodiment the mechanical alteration may include removal of at least a portion of the cavity contents.

In a still further embodiment, the method of the invention additionally comprises administering to the subject an antiresorptive agent for a time and at a concentration sufficient to substantially prevent resorption of the new bone produced due to the osteoblast activity. In one embodiment the antiresorptive agent may be administered contemporaneous with the administration of the bone anabolic agent. In another embodiment the antiresorptive agent is administered subsequent to the administration of the bone anabolic agent. In a further embodiment the administration of the antiresorptive agent may be commenced during administration of the bone anabolic agent and such administration may then be continued beyond the termination of administration of the bone anabolic agent.

In another embodiment of the invention a single agent may by administered having both bone anabolic and antiresorptive properties. Examples of such materials include, but are not limited to estrogen, strontium ranalate and selective estrogen receptor modulators (SERMS).

In an embodiment of the method of the invention the antiresorptive agent may be a calcitonin selected from the group consisting of human calcitonin, salmon calcitonin ("sCT"), eel calcitonin, elcatonin, pig calcitonin, chicken calcitonin, calcitonin gene related peptide (CGRP) and combinations thereof. In a preferred embodiment the antiresorptive agent is salmon calcitonin. Blood levels of calcitonin, when used as the antiresorptive agent, preferably range between about 5-500 pg/ml, more preferably between about 10-250 pg/ml and most preferably 20-50 pg/ml. Moreover, human dosage levels of the subject calcitonin agents necessary to achieve the above blood levels, in the case of, e.g., injectable formulations, may be those taught in the literature relating to the use of these materials as anabolic agents. Such dose may, but does not necessarily, range between about 5-200 µg/kg given once per day, more preferably between about 5-50 µg/kg and most preferably 8-20 µg/kg by weight of the pure drug, administered daily. Salmon calcitonin (sCT) administered by alternate routes, i.e., by nasal or oral administration, would require higher dosages than those discussed above.

Alternately, a variety of additional antiresorptive agents (i.e., other than the calcitonins) are useful with the method of the present invention. These include, generally, hormone replacement therapy (HRT) agents such as selective estrogen receptor modulators (SERMS), bisphosphonates, cathepsin-K inhibitors, strontium ranalate and various combinations thereof. Specific examples of additional antiresorptive agents include, but are not limited to, (1) PREMARIN® available from Wyeth Laboratories, which includes estrogen as the active ingredient. A typical accepted dosage is one 0.625 mg tablet daily; (2) ACTONEL® available from Proctor & Gamble, which includes, as its active ingredient, risedronate sodium. A typical accepted dosage is one 5 mg tablet daily or one 35 mg tablet weekly; (3) EVISTA® sold by Eli Lilly & Co. which includes raloxifene HCl as the active ingredient. A typical accepted dosage of this formulation is one 60 mg tablet taken daily; and (4) FOSAMAX® available from Merck Pharmaceuticals, which includes alendronate as the active ingredient. Typical dosages of this material are 10 mg/day or 70 mg/week.

Except where otherwise noted or where apparent from the context, dosages herein refer to the weight of the active compounds unaffected by pharmaceutical excipients, diluents, carriers or other ingredients, although such other ingredients are typically included in the variety of dosage forms useful in the method of the invention. Any dosage form (i.e., capsule, tablet, injection or the like) commonly used in the pharmaceutical industry is appropriate for use herein and the terms "excipient", "diluent" or "carrier" include such non-active ingredients as are typically included, together with active ingredients, in the industry. For example, typical capsules, pills, enteric coatings, solid or liquid diluents or excipients, flavorants, preservatives, or the like are included. Moreover, it is additionally noted that with respect to all of the dosages recommended herein, the attending clinician should monitor individual patient response, and adjust the dosage accordingly.

The antiresorptive agent may be administered orally, intravenously, intramuscularly, subcutaneously, via implant, transmucosally, rectally, nasally, by depot injection, by inhalation and pulmonary absorption or transdermally. Moreover, the antiresorptive agent may be administered once, a plurality of times, or over one or more extended periods. The antiresorptive agent may be administered orally, intravenously, intramuscularly, subcutaneously, via implant, transmucosally, rectally, nasally, by depot injection, by inhalation and pulmonary absorption or transdermally. Moreover, the antiresorptive agent may be administered once, a plurality of times, or over one or more extended periods.

The invention additionally provides a method of inducing bone formation in a subject suffering from diminished bone mass which comprises the steps of targeting for treatment at least one bone of the subject, wherein each targeted bone defines a bone marrow cavity therein. The bone marrow cavity contains a quantity of bone marrow and a plurality of osteoblasts. The method of the invention further comprises mechanically altering the contents of the bone marrow cavity to thereby stimulate and thus increase osteoblast activity therein. Thereafter, bone mass is increased within the cavity due to the increased osteoblast activity. The method additionally comprises administering to the subject at least one bone anabolic agent for a duration and at a concentration sufficient to raise blood levels of the anabolic agent within the subject above natural levels thereof and thereby prolong the mechanically induced osteoblast activity. The method then further comprises additionally administering, either (1) contemporaneous with, (b) overlapping with, or (3) subsequent to the administration of the bone anabolic agent, an antiresorptive agent for a duration and at a concentration sufficient to substantially prevent resorption of new bone produced due to the increased osteoblast activity achieved in accordance with the invention. As with the method described above, the mechanical alteration of the contents of the bone marrow cavity thus permits specific bones of the subject to be targeted for enhanced bone formation.

In one embodiment of the above-described method the bone anabolic agent may be selected from the group consisting of natural parathyroid hormone, a truncate of natural parathyroid hormone, an amidated truncate of natural parathyroid hormone, an amidated natural parathyroid hormone and combinations thereof. In one particular embodiment, the agent may be PTH-[1-34] in the free acid form, sold by Eli Lilly & Co. under the trademark FORTEO® (teriparatide). In a further embodiment the bone anabolic agent is an amidated truncate of natural parathyroid hormone and may be selected from among PTH[1-30]$NH_2$, PTH[1-31]$NH_2$, PTH[1-32]$NH_2$, PTH[1-33]$NH_2$, PTH[1-34]$NH_2$ and combinations thereof. A preferred choice for the bone anabolic agent is PTH[1-34]$NH_2$.

In a further embodiment of the invention a sufficient amount of an amidated truncate of natural parathyroid hormone is administered to the subject to achieve a pulsatile blood concentration thereof in the subject of between about 50 and 500 pg/ml, preferably between about 100-200 pg/mil and most preferably about 150 pg/ml. In the case of an injectable formulation, for example, the dose (in pure weight of the active hormone) given to a human subject, may be that taught in the literature relating to the bone anabolic activity of these various agents. Such dose may, but does not necessarily, range between about 10-200 μg per dose, more preferably between about 20-100 μg and most preferably between about 20-50 μg. When alternate delivery methods are used the dose may, but does not necessarily, range between about 10 μg-10 mg.

In a particular embodiment the antiresorptive agent is a calcitonin selected from among human calcitonin, salmon calcitonin, eel calcitonin, elcatonin, pig calcitonin, chicken calcitonin gene related peptide (CGRP) and combinations thereof. In one embodiment the antiresorptive agent is salmon calcitonin. It is preferred to achieve blood levels of salmon calcitonin, when it is used as the antiresorptive agent, of between about 5-500 pg/ml, more preferably between about 10-250 pg/ml and most preferably between about 20-50 pg/ml. To achieve the above-indicated serum levels daily dosages of the antiresorptive agent used in, e.g., injectable formulations, may range between about 5-200 μg (pure weight of the drug), more preferably between about 5-50 μg and most preferably between about 8-20 μg. When alternate delivery methods, i.e., other than injection, are used, the dose may range between about 5 μg-5 mg. Administration of the antiresorptive agent preferably continues for at least 3 months and more preferably between 12-24 months.

One embodiment of the invention comprises the use of any of the above described methods to form a sufficient amount of additional bone in a jaw region of the subject to provide an anchor for a dental implant implanted therein. Alternately, or additionally, any of the methods described above may be utilized to form a sufficient amount of additional bone in one or more targeted bones of the subject to permit secure anchoring of a prosthetic device thereto. Such prosthetic devices may include, but are not limited to, a prosthetic knee, shoulder or hip. In a further embodiment, any of the methods of the invention may be utilized to form a sufficient amount of additional bone at any location in the subject to serve as a secure anchor for a hollow, adjustable insert anchored thereto. Additionally, any of the methods of the invention may be used in targeting at least one vertebra for additional bone formation, wherein a sufficient amount of bone is added to the at least one vertebra such that the subject is substantially freed from chronic pain caused due to vertebral crush.

In a still further embodiment the invention provides a kit for fostering bone formation in at least one targeted bone of a subject in need of such bone formation. The kit comprises at least one container having therein at least one bone anabolic agent and a mechanical alteration device for altering contents of a bone marrow cavity in at least one targeted bone of a subject. In another embodiment the kit may additionally comprise an evacuation device for evacuating at least a portion of the contents from the bone marrow cavity. In a further embodiment the kit may additionally comprise at least one container having therein at least one antiresorptive agent.

In one embodiment of the kit of the invention, the bone anabolic agent is selected from among natural parathyroid hormone, a truncate of natural parathyroid hormone, an amidated truncate of natural parathyroid hormone, an amidated natural parathyroid hormone, and combinations thereof. In a preferred embodiment the bone anabolic agent is a truncate of natural parathyroid hormone. A preferred truncate for use as the agent is PTH[1-34] in the free acid form. Other preferred truncates include amidated truncates. The bone anabolic agent may thus be selected from among PTH[1-30]$NH_2$, PTH[1-31]$NH_2$, PTH[1-32]$NH_2$, PTH[1-33]$NH_2$, PTH[1-34]$NH_2$ and combinations thereof. In a specific embodiment the bone anabolic agent is PTH[1-34]$NH_2$.

In an additional embodiment of the kit of the invention the antiresorptive agent is a calcitonin selected from the group consisting of human calcitonin, salmon calcitonin, eel calcitonin, elcatonin, pig calcitonin, chicken calcitonin, calcitonin related gene peptide (CGRP) and combinations thereof. In a particular embodiment the antiresorptive agent is salmon calcitonin.

Although the present invention has been described in relation to particular embodiments thereof, many other variations and modifications and other uses will become apparent to those skilled in the art. The present invention, therefore, is not limited by the specific disclosure herein, but only by the claims.

What is claimed is:

1. A method of inducing bone formation in a subject suffering from diminished bone mass or bone trauma, said method comprising the steps of:
   (a) targeting for treatment at least one bone of said subject, each said targeted bone defining a bone marrow cavity therein, said bone marrow cavity containing a quantity of bone marrow and a plurality of osteoblasts;
   (b) mechanically altering the contents of said cavity by a surgical treatment thereof to induce an increase in osteoblast activity therein; and
   (c) administering to said subject at least one bone anabolic agent for a duration and at a concentration sufficient to raise blood levels of said anabolic agent within said subject above natural levels thereof to thereby prolong said mechanically induced increase in osteoblast activity, such that the mechanical alteration of the bone marrow cavity permits specific bones of said subject to be targeted by said method to permit enhanced bone formation therein, wherein steps (b) and (c) are performed in any order, but in sufficient time proximity that said elevated concentration of said bone anabolic agent and said mechanically induced increase in osteoblast activity at least partially overlaps.

2. The method of claim 1, wherein said bone formation is induced at a location of a long bone fracture in a bone of said subject to increase rapidity of healing of said fracture.

3. The method of claim 1, which further comprises reshaping or modeling at least one targeted bone of said subject by inducing additional bone formation in a controlled manner thereon.

4. The method of claim 1, wherein the bone anabolic agent is administered orally, intravenously, intramuscularly, subcutaneously, via implant, transmucosally, rectally, nasally, by depot injection, by inhalation and pulmonary absorption or transdermally.

5. The method of claim 1, wherein said bone anabolic agent also substantially reduces resorption of new bone produced due to said osteoblast activity.

6. The method of claim 5, wherein the bone anabolic agent is estrogen, strontium ranalate or a selective estrogen receptor modulator (SERM).

7. The method of claim 1, which further comprises administering to said subject an amount of Factor VII or Factor VIJA calculated to further increase said osteoblast activity.

8. A method of inducing bone formation in a subject suffering from diminished bone mass or bone trauma, said method comprising the steps of:
 (a) targeting for treatment at least one bone of said subject, each said targeted bone defining a bone marrow cavity therein, said bone marrow cavity containing a quantity of bone marrow and a plurality of osteoblasts;
 (b) mechanically altering the contents of said cavity by a surgical treatment thereof to induce an increase in osteoblast activity therein, whereby bone mass is correspondingly increased within said cavity;
 (c) administering to said subject at least one bone anabolic agent for a duration and at a concentration sufficient to raise blood levels of said anabolic agent within said subject above natural levels thereof and thereby prolong said mechanically induced osteoblast activity; and
 (d) additionally administering, either contemporaneous with or subsequent to the administration of said bone anabolic agent, an antiresorptive agent for a duration and at a concentration sufficient to substantially reduce resorption of new bone produced due to said osteoblast activity, such that the mechanical alteration of the bone marrow cavity permits specific bones of said subject to be targeted by said method to permit enhanced bone formation therein.

9. The method of claim 8, wherein the bone anabolic agent is selected from the group consisting of PTH[1-84] in the free acid form, PTH[-84]NH$_2$, PTH[1-34} in the free acid form, PTH[1-30]NH$_2$, PTH[1-31]NH$_2$, PTH[1-32]NH$_2$, PTH[1-33]NH$_2$, PTH[1-34]NH$_2$ and combinations thereof.

10. The method of claim 9, wherein a sufficient amount of said bone anabolic agent is administered to said subject to achieve a pulsatile blood concentration thereof in said subject of between about 50-500 pg/ml.

11. The method of claim 8, wherein said antiresorptive agent is a calcitonin selected from the group consisting of human calcitonin, salmon calcitonin, eel calcitonin, elcatonin, pig calcitonin, chicken calcitonin, and combinations thereof 12. The method of claim 11, wherein the antiresorptive agent is salmon calcitonin and wherein the salmon calcitonin is administered to said subject in an amount calculated to achieve a blood concentration thereof in said subject of between about 50-350 pg/ml.

\* \* \* \* \*